United States Patent [19]
DeMarsh

[11] Patent Number: 5,714,469
[45] Date of Patent: Feb. 3, 1998

[54] METHOD OF TREATING SEPSIS

[75] Inventor: Peter Lawrence DeMarsh, West Chester, Pa.

[73] Assignee: SmithKline Beecham Corporation, Philadelphia, Pa.

[21] Appl. No.: 299,777

[22] Filed: Sep. 1, 1994

[51] Int. Cl.$^6$ .......................... A61K 38/00; A61K 31/70; A61K 31/395; A61K 31/545

[52] U.S. Cl. .................. 514/15; 514/16; 514/17; 514/18; 514/40; 514/203; 514/210

[58] Field of Search .................. 514/15, 16, 17, 514/18, 40, 203, 210

[56] References Cited

FOREIGN PATENT DOCUMENTS 0 408 371 A1  1/1991  European Pat. Off. .

OTHER PUBLICATIONS

The Merck Index, Tenth Edition, abstract Nos. 1913, 2311 and 4251. (1983).

*Primary Examiner*—Kevin E. Weddington
*Attorney, Agent, or Firm*—Linda E. Hall; Stephen A. Venetianer; Edward T. Lentz

[57] ABSTRACT

The invention relates to the method of preventing and treating sepsis using (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2, 7,8 triaminooctanoyl-lysine [(pGlu-Glu-Asp)$_2$-Sub-(Lys)$_2$] alone or in conjunction with an anti-infective agent.

10 Claims, No Drawings

METHOD OF TREATING SEPSIS

FIELD OF INVENTION

This invention relates to the method of preventing and treating sepsis using (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine [(pGlu-Glu-Asp)$_2$-Sub-(Lys)$_2$] alone or in conjunction with an anti-infective agent.

BACKGROUND OF INVENTION

Sepsis, as used herein, is broadly defined to mean situations when the invasion of a host by a microbial agent is associated with the clinical manifestations of infection including but not limited to:

(1) temperature >38° C. or <36° C.; (2) heart rate >90 beats per minute; (3) respiratory rate >20 breaths per minute or $PaCO_2$<32 mm Hg; (4) white blood cell count >12,000/cu mm, <4,000/cu mm, or >10% immature (band) forms; (5) organ dysfunction, hypoperfusion, or hypotension. Hypoperfusion and perfusion abnormalities may include, but are not limited to lactic acidosis, oliguria, or an acute alteration in mental states. (Chest 1992; 101: 1644–1566).

Sepsis can occur in hospitalized patients having underlying diseases or conditions that render them susceptible to bloodstream invasion or in burn, trama or surgical patents. In many cases of sepsis, the predominant pathogen is *Escherichia coli*, followed by other Gram-negative bacteria such as the Klebsiella-Enterobacter-Serratia group and then Pseudomonas. Although comprising a somewhat smaller percentage of infection, Gram-positive microbes such as Staphylococcus and systemic viral and fungal infections are included by the term sepsis as used herein. The genitourinary tract is the most common site of infection, the gastrointestinal tract and respiratory tract being the next most frequent sources of sepsis. Other common foci are wound, burn, and pelvic infections and infected intravenous catheters.

A serious consequence of bacterial sepsis often is septic shock. Septic shock is characterized by inadequate tissue perfusion, leading to insufficient oxygen supply to tissues, hypotension and olgiuria.

Septic shock occurs because bacterial products react with cells and components of the coagulation, complement, fibrinolytic and bradykinin systems to release proteases which injure cells and alter blood flow, especially in the capillaries.

Microorganisms frequently activate the classical complement pathway, and endotoxin activates the alternative pathway. Complement activation, leukotriene generation and the direct effects of bacterial products on neutrophils lead to accumulation of these inflammatory cells in the lungs, release of their proteolytic enzymes and toxic oxygen radicals which damage the pulmonary endothelium and initiate the adult respiratory distress syndrome ("ADS"). ARDS is a major cause of death in patients with septic shock and is characterized by pulmonary congestion, granulocyte aggregation, haemorrhage and capillary thrombi.

Septic shock is a major cause of death in intensive care units. There are an estimated 200,000 cases per year of septic shock in the United States, and despite advances in technology (i.e., respiratory support) and antibiotic therapy, the mortality rate for septic shock remains in excess of 40%. In fact, mortality for established septic shock has decreased very little since the comprehensive description by Waisbren (*Arch. Intern. Med.* 88:467–488 (1951)). Although effective antibiotics are available, and there is an increased awareness of the septic shock syndrome, the incidence of septic shock over the last several decades has actually increased. With the appreciation that antimicrobial agents have failed to completely abrogate septic mortality, it is clear that other agents must be developed to be used alone or in conjunction with antimicrobials in order to rectify the deficiencies of current established therapy.

BRIEF DESCRIPTION OF THE INVENTION

This invention relates to a method of preventing or treating sepsis comprising administering to an animal, including humans, in need thereof an effective amount of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8triaminooctanoyl-lysine-(pGlu-Glu-Asp)$_2$-Sub-(Lys)$_2$.

This invention further relates to a method of preventing or treating sepsis comprising administering to an animal (including humans) in need thereof an effective amount of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine either before, in conjunction with or after an anti-infective agent.

DETAILED DESCRIPTION OF THE INVENTION

It is the object of this invention to provide a new method of treatment of sepsis comprising administering to an animal in need thereof, including humans, an effective amount of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine [(pGlu-Glu-Asp)$_2$-Sub-(Lys)$_2$ wherein Sub is diaminosuberic acid] alone or in combination with other anti-infective agents.

This invention further relates to a method of preventing sepsis comprising administering to an animal in need thereof an effective amount of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine alone or in combination with other anti-infective agents.

Known anti-infective agents include, without limitation, anti-microbial agents routinely used for the treatment of sepsis such as amino-glycosides (such as amikacin, tobramycin, netilmicin, and gentamicin), cephalosporins such as ceftazidime, related beta-lactam agents such as maxalactam, carbopenems such as imipenem, monobactam agents such as aztreonam; ampicillin and broad-spectrum penicillins, (e.g., penicillinase-resistant penicillins, ureidopenicillins or antipseudomonal penicillin or Augmentin) that are active against *P. aeruginosa*, Enterobacter species, indole-positive Proteus species, and Serratia. Also included within the definition of anti-infective agents are antifungal agents, amphotericin and the like as well as anti-vital agents such as famvir and acyclovir.

The compound is useful in the treatment of both humans and other animals such as dairy cattle, horses, calves or poultry.

(S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine has been described in U.S. patent application No. 08/001,905 incorporated by reference herein. It has been reported to stimulate granulocyte macrophage colony farming units (CFU-GM) (Pelus, L., et al. 1991. *Exp. Hematol.,* 19:487). It also increases serum colony stimulating activity. (King A., et al. *Exp. Hematol.* 19:481) peritoneal macrophage superoxide and candidacidal activity (Frey C., et al., *XI Congress of the International Society for Human and Animal Mycology,* p 151). The use of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine for the prevention and treatment of sepsis has not been reported. It has now been discovered that (S)-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-a-aspartyl]-L-threo-2,7,8 triaminooctanoyl-lysine significantly increases the survival of animals challenged with lethal sepsis causing organisms. Treatment with the compound of this invention, alone or in combination with an anti-infective agent prior to contemplated thoracic or abdominal surgery would be useful in reducing the likelihood of post-operative sepsis. It may also be used post-operatively for the treatment of sepsis caused by a variety of reasons as outlined previously.

To effectively treat a human or other animal (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine may be administered by injection in the dose range of about 1 to about 100 ng/kg, or orally in the dose range of about 1 to about 100 ng/kg body weight per day; if administered by infusion or similar techniques, the dose may be in the range of about 1 to about 100 ng/kg/day.

Depending on the patient's condition, the compound of this invention can be administered for prophylactic and/or therapeutic treatments. In therapeutic application, the compound is administered to a patient already suffering from a disease in an amount sufficient to cure or at least partially arrest the disease and its complications. In prophylactic applications, a composition containing (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine is administered to a patient not already in a disease state to enhance the patient's resistance. It may be given one day or one week prior to surgery, preferably one to two days prior to surgery. It may be administered parenterally or orally.

Single or multiple administrations of the compound can be carded out with dose levels and pattern being selected by the treating physician. In any event, a quantity of the compound of the invention sufficient to effectively treat the patient should be administered.

The compounds of this invention, may also be administered in conjunction with a conventional anti-infective as disclosed herein above, such a gentamicin, augmentin or ceftazidime. The particular anti-infective chosen should be one to which the infective organism is susceptible and is selected or modified during therapy as the infecting microrganism is more particularly identified.

Additionally, various adjunctive agents in the treatment of septic shock also may be useful in combination with the components of this invention. They include sympathomimetic amines (vasopressors) such as norepinephrine, epinephrine, isoproterenol, dopamine, and dobutamine; anti-inflammatory agents such as methylprednisolone anti-inflammatory agents such as indomethacin and phenylbutazone; and corticosteroids such as betamethasone, hydrocortisone, methylprednisolone, or dexamethasone; anti-coagulants such as heparin, anti-thrombin III or coumarin type drugs for certain conditions and schedules; diuretics such as furosemide or ethacrynic acid; and antagonist of opiates and beta-endorphins such as naloxone; an antagonist of tumor necrosis factor or of interleukin-1; phenothiazines; anti-histamines; glucagon; α-adrenergic blocking agents, vasodilators; plasma expanders; packed red blood cells; platelets; cryoprecipitates; fresh frozen plasma; bacterial permeability protein; clindamycin; and antibodies to (lipid A), the J5 mutant of *E. coli* or to endotoxin core glycolipids. Methods for preparing such antibodies are described widely in the literature.

One of the most important aspects in the treatment of the clinical septic shock syndrome is its apparently intractable resistance to the effects of a variety of highly potent antimicrobial agents. Despite the development of newer antimicrobial agents, the overall incidence of clinical sepsis has increased, and mortality remains unacceptably high, often approaching 60% of diagnosed patients. The discovery of the increased survival with the treatment of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine both prophylactically and after infection provides a new and useful therapy of sepsis.

The biological activity of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine was demonstrated by the following assays:

EXAMPLE 1

Rats.

Male Fischer 344 rats obtained from Taconic farms weighing 200 to 250 g. were utilized. The rats were housed 2 per cage in standard plastic caging and fed lab chow and water ad libitum.

(S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine was prepared by standard peptide synthesis procedures. The purity of the peptide was analyzed by high performance liquid chromatography (HPLC) and the structure confirmed by amino acid analysis and fast atom bombardment mass spectroscopy (FABMS). The compound was dissolved in DPBS containing 0.5% of heat inactivated autologus normal rat serum, then loaded into fourteen day Alza mini pumps. The rats were anethetisized and the pump implanted subcutaneously on the flank. Control animals were implanted with pumps loaded with dilution buffer.

*E. coli.*

A clinical isolate of *E. coli* isolated from sputum was utilized. The organisms were tested for antibiotic sensitivity by the disc-agar diffusion technique and found to be sensitive to gentamicin, ampicillin, cephalothin, chloramphenicol, kanamycin, tetracycline, trimethoprin/sulfamethoxazole and resistant to penicillin G, erythromycin, and vancomycin. The organism was animal passed in mice and subsequently recovered and plated onto MacConkey's agar. The reisolated organisms were grown overnight in brain-heart infusion broth, and then stored frozen at −70° C. The inoculate the fibrin clot, organisms from thawed stocks were inoculated into brainheart infusion broth and incubated overnight on a rotary shaker (120 rpm) an 37° C. The *E. coli* was harvested by centrifugation, washed 3X and finally resuspended in normal saline. The number or organisms was quantified by turbidimentry, and the concentration adjusted with normal saline. All inoculum sizes were based on viable counts determined by scoring colony forming units on MacConkeys agar.

Fibrin Clot.

The *E. coli* infected fibrin clots were made from a 1% solution of bovine fibrinogen (Type 1-S, Sigma) in sterile saline. The clot was formed by adding sequentially human thrombin (Hanna Pharma.) bacteria, and fibrinogen solution to 24 well plastic plates. Bacterial numbers of 2.0 to $3.0 \times 10^9$ were used in inoculate the fibrin clots. The resulting mixture was then incubated at room temperature for 30 minutes before implantation.

Animal Model.

The rats are anethetized with ketamine/xylazine (40 mg/kg/5 mg/kg) then the abdominal surfaced is shaved and a midline laporatomy performed. Bacterial peritonitis was induced by implanting a fibrin-thrombin clot containing *E. coli* into the abdominal cavity. After implantation the muscle layers were closed with 4-0 silk suture, and the wound closed with surgical staples. The animals were closely observed, any animals obviously moribound were euthanized.

Gentamicin.

Rats were treated subcutaneously with gentamicin sulfate (Elkins-Sinn, N.J.) 5 mg/kg twice a day for five days.

Statistics.

All continuously variable data are expressed as the percent survival from several pooled studies. The Fisher's Exact test was used to determine the statistical significance of the differences between the survival rates at 14 days. The differences between the groups were considered statistically significant at $p<0.05$.

The rats were prophylactically treated by subcutaneously implanted Alza pump starting on day—6 with (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine at either 0.1, 1.0, 10 or 100 ng/kg/day or dilution buffer. On day 0 the rats were implanted with an *E. coli* containing fibrin clot. Starting two hours after infection the rats were treated with gentamicin twice daily. The rats prophylactically treated with (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine at 0.1, 1.0, 10 or 100 ng/kg followed by gentamicin treatment all demonstrated significantly increases survival rates over the diluent treated control rats treated with gentamicin.

| Results | |
|---|---|
| Dose (ng/kg/day) | Survival (Alive/Dead) |
| Control | 34/49 |
| 0.1 | 32/8 |
| 1.0 | 34/6 |
| 10.0 | 29/11 |
| 100 | 33/7 |

EXAMPLE 2

Studies to determine the length of pretreatment necessary were done using prepared poly-L-lactide biodegradable polymer obtained from Burmingham Polymers following the procedure in J. of Microencapsulation 1990, Vol. 7, issue 3, pp. 347–355. In these studies the rats were infected with the single subcutaneous dose formulation of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine (10 ng/kg/day) on either day —6, day—3, day—1, 6 hours before infection, 2 hours before infection or 2 hours after infection. Control rats were dosed at the same time points with empty formulation. At time 0 the rats were infected with an *E. coli* containing fibrin-thrombin clot followed by twice a day gentamicin therapy (10 mg/kg/day) for 5 days. Survival at 14 days was ascertained. When the rats were treated with compound for six hours, two hours before infection or two hours after infection they did not show statistically significant protection. However, when they were phophylactically treated for either one, three, or six days the rats demonstrated statistically significant protection (day—1 p<0.03; day—3 p<0.002; day—6 p<0.001). As the rats were prophylactically treated for longer periods, the level of protection increased. However, as little as one day of pretreatment demonstrated a statistically significant increase in survival.

| Results Survival (Alive/Dead) | | |
|---|---|---|
| Pretreatment Time | Controls | Compound |
| −1 Day | 8/17 | 16/9 |
| −3 Days | 6/19 | 19/6 |
| −6 Days | 14/11 | 22/3 |

EXAMPLE 3

The rats were pretreated with a single subcutaneous dose formulation (as described in Example 2) of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine on day—6 to infection. The rats were infected with a dose *E. coli* in the fibrin-thrombin clot that elicits ten to twenty percent survival in the control group. Survival 14 days after infection was ascertained.

| Results | |
|---|---|
| Dose (ng/kg/day) | Survival (Alive/Dead) |
| Control | 6/28 |
| 1.0 | 8/17 |
| 3.3 | 12/13 |
| 10 | 16/9 |
| 33 | 11/14 |

EXAMPLE 4

Studies to determine if oral pretreatment with (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine could protect rats infected with an *E. coli* containing fibrin-thrombin clot were done. In these studies the rats were orally dosed by placing the compound at 10, 33, 100 or 333 ng/kg on a commercially prepared tablet (Bio-Serv®, A. Holton Ind. Frenchtown, N.J.) then allowing the rats to eat the tablet. Because this tablet is high in fat and sucrose the rats like the taste and all the rats eat the tablet within thirty minutes. After infection most of the animals are too sick to eat so post infection dosing was variable. The rats were given gentamicin twice a day (10 mg/kg/day) for 5 days. Survival at day 14 was ascertained.

| Results | |
|---|---|
| Dose (ng/kg/day) | Survival (Alive/Dead) |
| Control | 11/14 |
| 10 | 23/2 |
| 33 | 22/3 |
| 100 | 18/7 |
| 333 | 13/12 |

EXAMPLE 5

The rats were prophylactically treated with the biodegradable microsphere formulation of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine, six days prior to infection with E. coli in a fibrin-thrombin clot. Starting two hours after infection, the rats were injected subcutaneously with ceftazidime 10 mg/kg twice a day for 14 days.

| Results | |
|---|---|
| Dose (ng/kg/day) | Survival (Alive/Dead) |
| Control | 12/13 |
| 0.1 | 17/8 |
| 1.0 | 19/6 |
| 10.0 | 21/4 |
| 100 | 16/9 |

EXAMPLE 6

Studies evaluating the single dose subcutaneous formulation of (S)-5-oxo-L-prolyl-L-α-glutamyl-L -α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine in the rat model of Staph. aureus, gram-positive were done. The rats were prophylactically treated on day—6 with the single subcutaneous does formulation of compound. On day 0 the rats were infected with an E. coli containing fibrin-thrombin clot followed by twice a day gentamicin therapy (10 mg/kg/day). In this model, when the rats are not treated with gentamicin all the animals are dead by day two. Control rats were dosed with empty formulation. The rats dosed with 0.1, 1.0 or 10 ng/kg/day of SK&F 107647 followed by gentamicin therapy demonstrated statistically significantly increased protection over gentamicin alone (0.1 p<0.01; 1.0 p<0.01; 10 p<0.001).

| Results | |
|---|---|
| Dose (ng/kg/day) | Survival (Alive/Dead) |
| Control | 9/16 |
| 0.1 | 18/7 |
| 1.0 | 18/7 |
| 10.0 | 21/4 |
| 100.0 | 11/14 |

I claim:

1. A method of treating sepsis comprising administering to an animal in need thereof an effective amount of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine.

2. A method according to claim 1 wherein said effective amount is from about 1.0 to about 100 ng/kg/day.

3. The method according to claim 1 wherein (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine is administered orally.

4. A method of treating sepsis comprising administering to an animal in need thereof an effective amount of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine in conjunction with an effective amount of an anti-infective agent.

5. A method according to claim 4 wherein the anti-infective agent is selected from the group consisting of gentamicin, augmentin or ceftazidime.

6. A method for the prevention of sepsis comprising administering to an animal in need thereof an effective amount of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine.

7. A method according to claim 6 wherein the effective amount is from about 1.0 to about 100 ng/kg/day.

8. The method according to claim 6 wherein (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine is administered 1 to 2 days prior to surgery.

9. A method for the prevention of sepsis comprising administering to an animal in need thereof an effective amount of (S)-5-oxo-L-prolyl-L-α-glutamyl-L-α-aspartyl-$N^8$-(5-amino-1-carboxypentyl)-8-oxo-$N^7$-[N-[N-(5-oxo-L-prolyl)-L-α-glutamyl]-L-α-aspartyl]-L-threo-2,7,8 triaminooctanoyl-lysine in conjunction with an effective amount of an anti-infective agent.

10. A method according to claim 9 wherein the anti-infective agent is selected from the group consisting of gentamicin, augmentin or ceftazidime.

* * * * *